United States Patent [19]

Suhajda

[11] Patent Number: 4,703,155

[45] Date of Patent: Oct. 27, 1987

[54] ELECTRIC FOGGER

[75] Inventor: John I. Suhajda, Racine, Wis.

[73] Assignee: S. C. Johnson & Son, Inc., Racine, Wis.

[21] Appl. No.: 947,712

[22] Filed: Dec. 30, 1986

[51] Int. Cl.$^4$ .......................... A01M 13/00; H05B 1/02
[52] U.S. Cl. ..................................... 219/271; 219/272; 219/275; 219/518; 219/432; 43/129; 422/305
[58] Field of Search ............... 219/271, 272, 273, 274, 219/275, 276, 518, 432, 433; 422/305, 306, 125; 239/135, 136, 51.5, 53-60; 43/129

[56] References Cited

U.S. PATENT DOCUMENTS

| | | | |
|---|---|---|---|
| 1,990,338 | 2/1935 | Lippert | 219/271 |
| 2,543,052 | 2/1951 | Park | 219/432 |
| 4,156,456 | 5/1979 | Müller | 219/518 |
| 4,571,485 | 2/1986 | Spector | 219/274 |

FOREIGN PATENT DOCUMENTS 260643  10/1928  Italy ..................... 219/275

Primary Examiner—E. A. Goldberg
Assistant Examiner—Teresa Walberg

[57] ABSTRACT

A disposable canister for use in an electric fogger includes a container to hold a fog-producing material which is constructed of a material capable of transferring heat from a heat source to the fog-producing material, an insert secured in the container to close the container and having a dome with a discharge port to allow the release of a fog, and a cap secured to the container and having an opening which overlies the discharge port of the insert to allow the release of a fog and one or more lugs which serve to activate an electric fogger when placed in the housing of the electric fogger. The cap of the disposable canister also includes outwardly extending rims which seat on the housing of the electric fogger and in conjunction with the lugs of the cap serve to lock the canister into the housing. The invention precludes the escape of any fog from the closure seal between the container and the cap into the housing of the electric fogger and provides for fully efficient use of the fog-producing material.

6 Claims, 4 Drawing Figures

1

ELECTRIC FOGGER

FIELD OF INVENTION

This invention relates generally to an electric fogger apparatus for fogging materials such as insecticides, deodorants, perfumes, disinfectants, and air fresheners. In particular, this invention relates to an electric fogger disposable canister for containing an insecticide for fogging for use in conjunction with a housing of the electric fogger whereby upon insertion of the canister into the housing of the electric fogger the canister simultaneously activates the electric fogger and locks the canister into position in the electric fogger.

BACKGROUND OF INVENTION

A wide variety of electric devices are known in the art for dispensing of insecticides. Such devices are disclosed in U.S. Pat. No. 4,657,504, filed June 20, 1986, in the name of John I. Suhajda, which is incorporated in its entirety herein by reference. This application discloses a novel electric fogger generally comprising a disposable canister containing a fog-producing material and a housing. The electric fogger is activated by insertion of the disposable canister into the housing and rotating the canister which simultaneously activates the electric fogger and locks the canister into position, and then automatically turns the fogger off after completion of the fogging of the fog-producing material. This application also discloses novel disposable canisters for use in the electric fogger comprising generally a container which holds a fog-producing material and a cap to cover the container having an opening to allow release of a fog and having at least one lug extending from the cap for activating the electric fogger.

The disposable canisters disclosed in U.S. Pat. No. 4,675,504 have been found to be quite useful in dispensing insecticides and other fog-producing materials. However, in certain applications, the disposable canister constructions may allow the fog to escape from the closure seal between the container and the cap into the housing of the electric fogger. Escape of such fog is undesirable as it precludes efficient use of all of the fog-producing material. The present invention has solved this problem as will be more apparent hereinafter.

PRIMARY OBJECTS AND SUMMARY OF THE INVENTION

It is a primary object of the invention to provide a disposable canister for use in an electric fogger which retains a fog-producing material from contact by the user and which allows the fog-producing material to evaporate to the environment of use through an opening in the canister.

It is a further primary object of the invention to provide a disposable canister for use in an electric fogger which generally comprises a container, an insert having a dome with a discharge port to allow release of a fog which is fitted to the container and a cap secured to the container enclosing the insert and having an opening overlying the discharge port of the insert to allow for release of a fog to the environment of use whereby the insert prevents the escape of any fog from the closure seal between the container and the cap into the housing of the electric fogger.

It is a further object of the invention to provide a disposable canister for use in an electric fogger whereby upon insertion of the canister in the housing of the electric fogger the canister has means for activating the fogger and simultaneously locks the canister into the housing of the electric fogger.

It is an object of the invention to provide a disposable canister containing a fog-producing material for use in an electric fogger which is simple in construction and easy to use.

The disposable canister of the invention comprises a container to hold a fog-producing material which is constructed of a material capable of transferring heat from a heat source to the fog-producing material, an insert secured in the container to close the container and having a dome with a discharge port to allow the release of a fog, and a cap secured to the container and having an opening which overlies the discharge port of the insert to allow the release of a fog and one or more lugs which serve to activate an electric fogger when placed in the housing of the electric fogger. The cap of the disposable canister also includes outwardly extending rims which seat on the housing of the electric fogger and in conjunction with the lugs of the cap serve to lock the canister into the housing. The invention precludes the escape of any fog from the closure seal between the container and the cap into the housing of the electric fogger and provides for fully efficient use of the fog-producing material. The canister of the present invention provides for the simultaneous activation of the electric fogger and the locking of the canister into the housing of the electric fogger.

As used in the present invention, the term "fog-producing material" means a composition which evaporates upon heating or which undergoes a chemical reaction or decomposition of at least one component to produce a fog or aerosol to carry an active agent to the atmosphere. Examples of fog-producing materials include insecticides, repellants, perfumes, deodorants, disinfectants, etc. Preferred fog-producing materials are disclosed in U.S. Pat. No. 4,163,038.

BRIEF DESCRIPTION OF THE DRAWINGS

Other objects, advantages, and novel features of the present invention will become apparent from the following detailed description of the invention when considered in conjunction with the accompanying drawing, in which like reference numerals designate like parts throughout the figures thereof, and wherein.

DETAILED DESCRIPTION OF THE INVENTION

Figure 1:
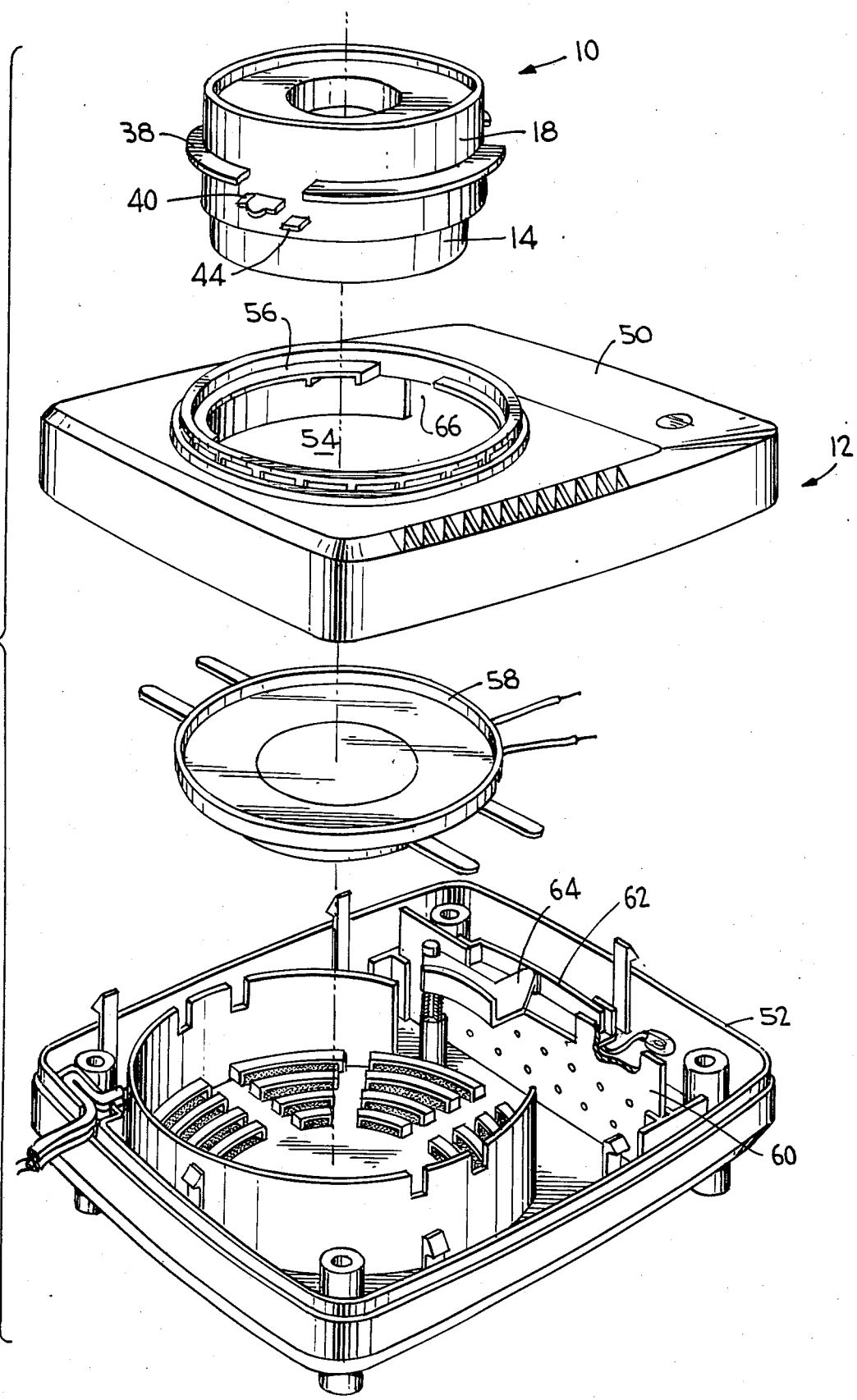
FIG. 1 is an exploded view showing the disposable canister and housing of an electric fogger.

Referring to FIG. 1, an electric fogger is shown comprising a disposable canister 10 constructed according to the present invention and a housing 12. A detailed description of housing 12 and the operation of canister 10 in housing 12 is disclosed in application Ser No. 876,584, filed June 20, 1986, now U.S. Pat. No. 4,675,504 which is incorporated herein by reference.

Figure 2:
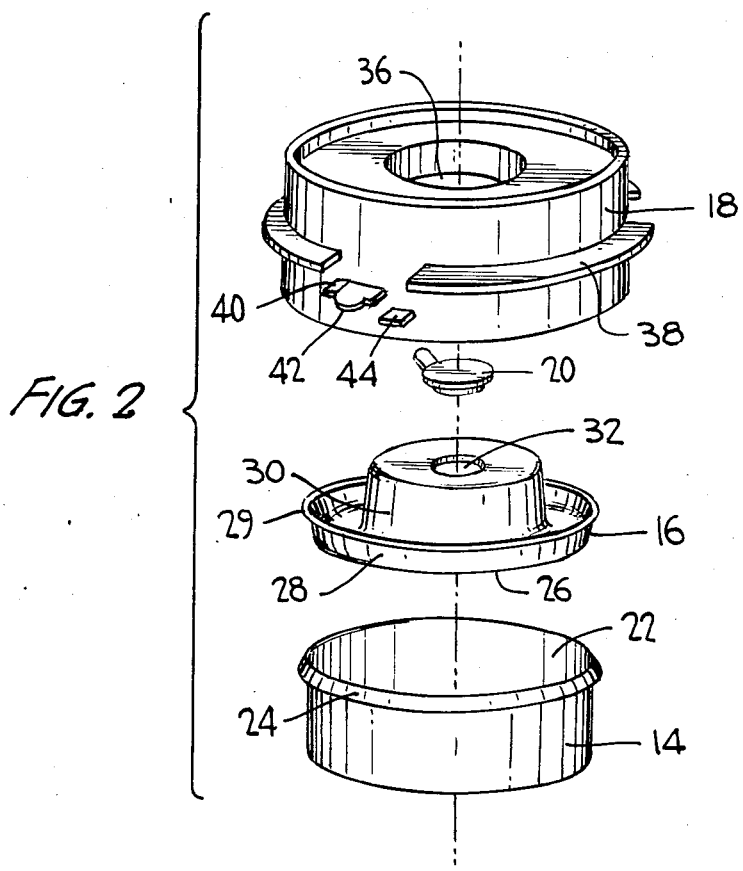
FIG. 2 is an exploded view of the disposable canister.
Figure 3:
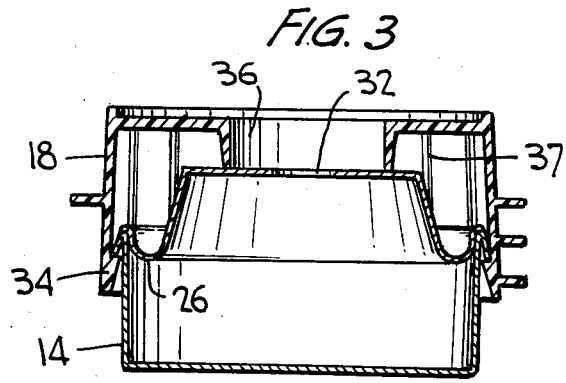
FIG. 3 is a cross-section of the disposable canister of FIG. 1.
Figure 4:
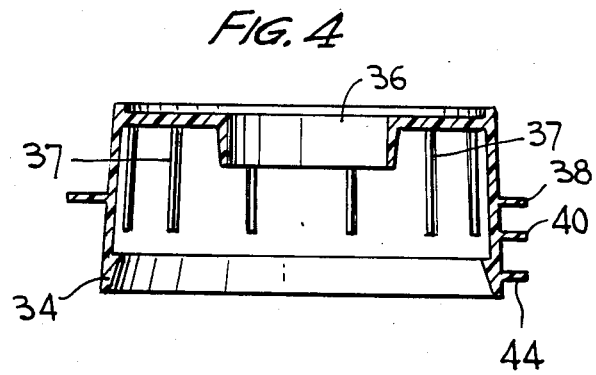
FIG. 4 is a cross-section of the cap of the disposable canister of FIG. 2.

Referring to the drawing, canister 10 includes a container 14, an insert 16, and a cap 18. A closure means 20, as shown in FIG. 2, may also be used to close the opening in the canister until use. The canister may contain any suitable fog-producing material known in the art such as an insecticide, a deodorant, a perfume, a disinfectant, or an air freshener for dispensing upon exposure to heat.

Container 14 has an open top 22 and lip 24 surrounding the periphery of the container for engaging an annular ledge 34 of cap 18 for securing cap 18 to the container. The container is made of a material capable of receiving heat and transferring the heat to the fog-producing material contained therein, and is preferably made of a lightweight metal although any other suitable material may be used.

Insert 16 fits tightly into container 14 to close opening 22 of container 14 and prevent the escape of fog from the closure seal between cap 18 and container 14. Insert 16 includes a base 26 having a hub 28 and dome 30. Hub 28 has an annular ledge 29 which seats on the peripheral edge of container 14. Hub 28 fits in container 14 adjacent to the inner walls of container 14. Dome 30 has a discharge port 32 to allow the release of a fog. Dome 30 also serves to direct the fog to discharge port 32 for release to the environment of use while concurrently preventing any substantial spitting of any unevaporated insecticide.

Cap 18 is preferably made of plastic by conventional molding processes. After insertion of insert 16 into container 14, container 14 is attached to cap 18 by means of lip 24 which catches on ledge 34 on the inside of cap 18. Cap 18 includes an opening 36 which overlies discharge port 32 to allow release of a fog. Cap 18 further includes a plurality of detents 37 extending outwardly from the interior wall of cap 18 and which seat on ledge 29.

Cap 18 further includes collars 38 extending outwardly from the cap for seating on flanges 56 of the housing 12 of the electric fogger as fully described in application Ser. No. 876,584. Further, cap 18 includes lugs 40 extending outwardly from the cap for activating the electric fogger and locking the canister into housing 12. Lugs 40 further include nipples 42 protruding from the lugs for activating the electric fogger by contacting an electrical switch means in the housing. Cap 18 also has a second set of lugs 44 extending outwardly from cap 18 and constructed and arranged below lugs 40. Lugs 44 are provided to activate a second electrical switch means in housing 12 depending on the activation and timing means used by the electric fogger.

A closure means 20 may be used to close discharge port 32 prior to use of canister 10 and to retain the fog-producing material in canister 10. Closure means 20 may be any conventional material. A preferred material is a meltaway polystyrene label which is advantageous because it does not require user contact with the label. The meltaway polystyrene label has an adhesive on one side for attachment to dome 30. Upon heating of the canister, the label will melt away opening discharge port 32 for release of a fog. Other conventional closure means may be used such as paper or polymer labels adhesively attached to dome 30 for manual removal by the user.

Generally, housing 12 is comprised of a top member 50 and a base member 52 capable of receiving and replaceably holding the disposable canister 10. Top member 50 includes an opening 54 for receiving and replaceably holding canister 10 having flanges 56 upon which collars 38 seat. The housing contains a heating means, e.g. a hot plate 58, for heating the fog-producing material in the canister 10; a printed circuit board 60 containing an electrical switch 62 for activating the heating means and a timer which automatically turns the heating means off after a predetermined period of time; and a pivoting cam 64 adapted to engage the electrical switch on the printed circuit board to allow electricity to flow to the heating means wherein the pivoting cam 64 engages the electrical switch 62 in response to contact from a lug 40 on the canister upon insertion and rotation of the canister in the housing. A more detailed description of the housing 12 and the operation of the electric fogger is set forth in application Ser. No. 876,584.

In use, the canister 10 is inserted into the housing 12 by inserting lugs 40 through openings 66 in housing 12 and collars 38 seat on flanges 56. The canister is rotated approxiamtely 1/6th of a turn whereby one of the lugs 40 will activate the electric fogger by contacting pivoting cam 64 which in turn contacts electrical switch 62 on the printed circuit board 60 to close the electrical circuit and turn the fogger on and activate a timing means. Lugs 40 in conjunction with collars 38 and flanges 56 also serve to lock the canister 10 into the housing 12.

The above-described invention provides a disposable canister for use in an electric fogger which is inexpensive to manufacture and easy and safe to use. The canister avoids user contact with the fog-producing material and allows the user to activate the fogger with the canister. While a preferred embodiment of the canister has been described in detail above, various modifications and variations of the invention are possible in light of the above teachings. It is, therefore to be understood that within the scope of the appended claims the invention may be practiced otherwise than as above-described.

It is claimed:

1. A fog-producing disposable canister for use in an electric fogger comprising:
   (1) a container having an open top which holds a fog-producing material and which is constructed of a material which will transfer heat from a heat source to said fog-producing material;
   (2) an insert secured in said container to close said open top and having a dome with a discharge port to allow the release of a fog; and
   (3) a cap attached to said container for covering said container having an opening overlying said discharge port of said insert to allow the release of a fog and having at least one lug extending from said cap for activating said electric fogger.

2. A fog-producing disposable canister according to claim 1 wherein said discharge port is closed prior to use by a closure means.

3. A fog-producing disposable canister according to claim 2 wherein said closure means comprises a meltaway label.

4. A fog-producing disposable canister according to claim 1 wherein said cap has a first set of lugs extending outwardly from said cap to activate a power source in said electric fogger and a second set of lugs constructed and arranged either above or below said first set of lugs to activate a timer means in said electric fogger whereby said fogger is operated for a predetermined period of time.

5. An electric fogging apparatus comprising:
   (a) a housing;
   (b) a canister for removable insertion into said housing comprising (1) a container having an open top which holds a fog-producing material and which is constructed of a material which will transfer heat from a heat source to said fog-producing material;

(2) an insert secured in said container to close said open top and having a dome with a discharge port to allow the release of a fog; and (3) a cap attached to said container for covering said container having an opening overlying said discharge port of said insert to allow the release of a fog and having at least one lug extending from said cap for activating said electric fogger;

(c) a means on said housing for receiving and replaceably holding said canister in said housing;

(d) an electrical heating means in said housing for heating said canister in said housing;

(e) an electrical timing means within said housing which controls said heating means whereby said heating means is operated for a predetermined period of time; and (f) an electrical switch means constructed and arranged with said timing means and said heating means for activating said timing means and said heating means, said switch means being activated by one of said lugs on said canister upon insertion and rotation of said canister in said receiving and holding means of said housing;

thereby heating said canister, the heat being transferred to said fog-producing material to produce a fog which is released to an environment of use through the discharge port of said insert and the opening in said canister cap.

6. An electric fogging apparatus comprising:

(a) a housing consisting of a base member and a top member;

(b) a disposable canister for removable insertion into said housing comprising (1) a container having an open top which holds a fog-producing material and which is constructed of a material which will transfer heat from a heat source to said fog-producing material;

(2) an insert secured in said container to close said open top and having a dome with a discharge port to allow the release of a fog;

(3) a closure means attached to said insert to close said discharge port until a fog is to be released; and (4) a cap attached to said container for covering said container having an opening overlying said discharge port of said insert to allow the release of a fog and having at least one lug extending from said cap for activating said electric fogger;

(c) an opening in said top member of said housing for receiving and replaceably holding said disposable canister said opening being bounded by at least one flange, said flange having at least one space for receipt of a lug from said canister;

(d) an electric hot plate secured in the base of said housing under said opening in said housing for supporting and heating said disposable canister;

(e) a printed circuit board located in said housing including (1) an electrical switch comprising a leaf spring and a contact whereby said leaf spring contacts the contact to close the electrical circuit allowing the flow of electricity to said hot plate; and (2) a timing means whereby said hot plate is operated for a predetermined period of time; and (f) a pivoting cam in said housing constructed and arranged to engage simultaneously one of said lugs on said canister upon insertion and rotation of said canister in said opening of said housing and said electrical switch means to activate said hot plate;

thereby heating said canister, the heat being transferred to said fog-producing material to produce a fog which is released to an environment of use through the discharge port of said insert and the opening in said canister cap.

* * * * *